(12) United States Patent
Kushner et al.

(10) Patent No.: US 9,938,368 B2
(45) Date of Patent: Apr. 10, 2018

(54) BIO-INSPIRED METHOD TO OBTAIN MULTIFUNCTIONAL DYNAMIC NANOCOMPOSITES

(71) Applicant: The Regents of the University of California, Oakland, CA (US)

(72) Inventors: Aaron M. Kushner, Solana Beach, CA (US); Zhibin Guan, Irvine, CA (US); Gregory Williams, San Clemente, CA (US); Yulin Chen, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/383,038

(22) PCT Filed: Mar. 7, 2013

(86) PCT No.: PCT/US2013/029723
§ 371 (c)(1),
(2) Date: Sep. 4, 2014

(87) PCT Pub. No.: WO2013/134569
PCT Pub. Date: Sep. 12, 2013

(65) Prior Publication Data
US 2015/0038649 A1 Feb. 5, 2015

Related U.S. Application Data

(60) Provisional application No. 61/608,045, filed on Mar. 7, 2012, provisional application No. 61/608,029, filed on Mar. 7, 2012.

(51) Int. Cl.
| | | |
|---|---|---|
| *C07F 7/02* | (2006.01) | |
| *C08F 293/00* | (2006.01) | |
| *C08K 3/36* | (2006.01) | |
| *C08G 83/00* | (2006.01) | |
| *C08L 51/10* | (2006.01) | |
| *C08L 101/02* | (2006.01) | |
| *C08F 292/00* | (2006.01) | |

(52) U.S. Cl.
CPC .............. *C08F 293/00* (2013.01); *C07F 7/02* (2013.01); *C08F 292/00* (2013.01); *C08F 293/005* (2013.01); *C08G 83/008* (2013.01); *C08K 3/36* (2013.01); *C08L 51/10* (2013.01); *C08L 101/02* (2013.01); *C08F 2438/01* (2013.01)

(58) Field of Classification Search
CPC .. C08F 292/00; C08F 293/00; C08F 293/005; C08F 2438/01; C07F 7/02; C08G 83/008; C08K 3/36; C08L 101/02; C08L 51/10
See application file for complete search history.

(56) References Cited

FOREIGN PATENT DOCUMENTS

| WO | 1999042528 A2 | 8/1999 |
|---|---|---|
| WO | 2007069765 | 6/2007 |

OTHER PUBLICATIONS

Yin, M. et al. Journal of Polymer Science Part A: Polymer Chemistry vol. 43 pp. 1873-1882 (Mar. 2005).*
A. Miserez, T. Schneberk, C. Sun, F. W. Zok, J. H. Waite, The Transition from Stiff to Compliant Materials in Squid Beaks, Science 2008, 319, 1816.
J. R. Capadona, K. Shanmuganathan, D. J. Tyler, S. J. Rowan, C. Weder, Stimuli-Responsive Polymer Nanocomposites Inspired by the Sea Cucumber Dermis, Science 2008, 319, 1370.
M. W. Urban, Dynamic Materials: The Chemistry of Self-healing, Nat. Chem. 2012, 4, 80.
S. R. White, N. R. Sottos, P. H. Geubelle, J. S. Moore, M. R. Kessler, S. R. Sriram, E. N. Brown, S. Viswanathan, Autonomic healing of polymer composites, Nature 2001, 409.
X. Chen, M. A. Dam, K. Ono, A. Mal, H. Shen, S. R. Nutt, K. Sheran, F. Wudl, A Thermally Re-mendable Cross-Linked Polymeric Material, Science 2002, 295, 1698.
M. Burnworth, L. Tang, J. R. Kurnpfer, A. J. Duncan, F. L. Beyer, G. L. Fiore, S. J. Rowan, C. Weder, Optically healable supramolecular polymers, Nature 2011, 472, 334.
P. Cordier, F, Tournilhac, C. Soulie-Ziakovic, L. Leibler, Self-healing and Thermoreversible Rubber from Supramolecular Assembly, Nature 2008, 451, 977.
Martin D. Hager, et al., "Self-Healing Materials", Adv. Mater. 2010, vol. 22, pp. 5424-5430.
I. De Graeve, et al., "A coating combination of self-healing polymers and corrosion inhibitors for active corrosion protection of metals", in Book of Abstracts, 2nd "MUST"WORKSHOP on Self-Healing Coatings: Effectiveness and Imelementation, Jun. 28, 2010. Noordwijk, The Netherlands.
Holger Kautz, et al. "Cooperative End-to-End and Lateral Hydrogen-Bonding Motifs in Supramolecular Thermoplastic Elastomers", Macromolecules. 2006, vol. 39, No. 13, pp. 4265-4267.
B. J. Blaiszik, et al., "Self-Healing Polymers and Composites", Annu. Rev. Mater. Res. 2010, vol. 40, pp. 179-211.
International Preliminary Report and Written Opinion dated Jun. 21, 2013 in connection with related PCT Application No. PCT/US2013/029723.
Linbo Wu, et al; Synthesis, Properties, and Light-Induced Shape Memory Effect of Multiblock Polyesterurethanes Containing Biodegradable Segments and Pendant Cinnamamide Groups; Biomacromolecules 2011, 12: 235-241.

(Continued)

*Primary Examiner* — Irina S Zemel
*Assistant Examiner* — Jeffrey S Lenihan
(74) *Attorney, Agent, or Firm* — Berliner & Associates

(57) ABSTRACT

A method for a polymeric or nanocomposite material. The method includes assembling a multiphase hard-soft structure, where the structure includes a hard micro- or nano-phase, and a soft micro- or nano-phase that includes a polymeric scaffold. In the method, the polymeric scaffold includes dynamically interacting motifs and has a glass transition temperature ($T_g$) lower than the intended operating temperature of the material.

14 Claims, 5 Drawing Sheets

(56) References Cited

OTHER PUBLICATIONS

Praveen Agarwal, et al., Shape-Memory Polymers: Nanoparticle Netpoints for Shape-Memory Polymers; Angew. Chem. Int. Ed. 2011, 50: 8670-8673.

Schnell, et al., "Quadruple Hydrogen Bonds of Ureidopyrimidinone moieties Investigated in the Solid State by 1H Double-Quantum Mas NMR Spectroscopy", Physical Chemical Chemical Physics, Royal Society of Chemistry, Cambridge, GB,vol. 4, No. 15, Aug. 1, 2002, pp. 3750-3758.

Ten Cate A Tessa, et al., "Hydrogen-bonded supramolecular polymers with tunable material properties": Polymer Preprints, American Chemical Society, US, vol. 44, No. 1, Jan. 1, 2003, pp. 618-619.

Aaron M. Kushner, et al., "A Biomimetic Modular Polymer with Tough and Adaptive Properties", Journal of the American Chemical Society, vol. 131, No. 25, Jul. 1, 2009, pp. 8766-8768.

Katia Paderni, et al., Shape-memory polymer networks from sol-gel cross-linked alkoxysilane-terminated poly ([epsilon]-caprolactone); Journal of Materials Science, Kluwer Academic Publishers, BO vol. 47, No. 10, Feb. 8, 2012, pp. 4354-4362.

* cited by examiner

BIO-INSPIRED METHOD TO OBTAIN MULTIFUNCTIONAL DYNAMIC NANOCOMPOSITES

STATEMENT REGARDING FEDERALLY SPONSORED RESEARCH OR DEVELOPMENT

This invention was made with Government support under Grant Nos. DMR-1217651 from the National Science Foundation and DE-FG02-04ER46162 from the Department of Energy. The Government has certain rights in this invention.

BACKGROUND

Field of the Invention

The invention relates to nanocomposite materials and methods of making thereof.

Related Art

The market for aerospace composites is expected to exceed $50 billion in 2014. These materials make up more than 50% of the latest generation of aircraft because of their advantageous low density, excellent combination of stiffness and toughness, and resistance to corrosion when compared to conventional aluminum alloys (1). Unfortunately, these materials, which took decades to become accepted by the aerospace industry, are running into limitations inherent to their composition and production methods, such as poor high-temperature tolerance and expensive, complicated processing. Nanocomposites present a potential route to both improved properties and simpler processing, as well as access to new and multiple functionalities (2), and are the key to unlocking the next revolution in aerospace materials technology.

A nanocomposite is a multiphase solid material where one of the phases has one, two or three dimensions of less than 100 nm, or structures having nano-scale repeat distances between the different phases that make up the material. In mechanical terms, nanocomposites differ from conventional composites due to the exceptionally high surface to volume ratio of the reinforcing phase and/or its exceptionally high aspect ratio. The mechanical, electrical, thermal, optical, electrochemical, and catalytic properties of the nanocomposite will differ markedly from that of the component materials. This "emergent" (the whole being greater than the sum of the parts) functionality property places nanocomposites in the optimal design space to provide a solution to both the "materials-by-design" and "multifunctionality" requirements for the next generation of synthetic engineering materials (3,4).

Synthetic nanocomposites are an important research target in materials science. The use of nanoparticle-rich materials long predates the understanding of the physical and chemical nature of these materials. From the mid-1950s nanoscale organo-clays have been used to control flow of polymer solutions (e.g. as paint viscosifiers) or the constitution of gels (e.g. as a thickening substance in cosmetics, keeping the preparations in homogeneous form). By the 1970s polymer-clay nanocomposites were commercially viable commodity materials. This successful system is nonetheless limited to low nano-object volume fractions, due to synthesis and processing obstacles that have thus far prevented the full realization of the potential engineering benefits and game-changing technologies presented by nanocomposites.

Nanocomposites are nature's universal materials-by-design solution. Biological nanocomposites may possess >95% inorganic volume fraction in <5% polymer matrix, as in the case of abalone nacre, giving this material both strength and toughness (5). Biological nanocomposites may also possess zero inorganic component, as in the case of spider dragline silk, which is among the toughest and strongest materials known, as a result of nanoscale reinforcement by organic crystallites. The modular design of biological nanocomposites enables a wide range of mechanical properties to be obtained from the same starting components and manufacturing process (6). For example, stiff and tough bone and strong and extensible tendon vary only in their degree of inorganic nanoscale reinforcement. The dynamic nature of the self-assembly processes makes the resulting materials adaptive and highly tolerant of minor manufacturing flaws. Critically, the modular design and universal process capability of biological-nanocomposites enables the facile production of mechanical property gradients, for example at the interface of bone and tendon, minimizing interfacial stresses, a key failure mechanism in synthetic materials. An extreme example of this effect is seen in the squid beak, the hardest natural substance at its edge, which must bond to the soft and flexible squid body (7). Finally, biological nanocomposites possess emergent multifunctionality, such as the ability to change mechanical properties in response to environmental stimuli, as in the case of the Sea Cucumber dermis (8).

The ability to spontaneously heal injury is another key emergent functionality found in biological nanocomposites that increases the survivability and lifetime of most plants and animals. In sharp contrast, synthetic materials usually fail after damage or fracture.

For decades, scientists and engineers have dreamed of developing self-healing materials to improve the safety, lifetime, energy efficiency, and environmental impact of manmade materials (9). The first successful demonstration of a spontaneously self-healing (requiring no external input or trigger beyond the damage itself) involves micro-encapsulated healing agents and catalysts embedded in a conventional polymer matrix (10). While this approach is very effective for the initial damage-healing cycle, further damage in an already healed region is not reversible due to prior consumption of the healing agents. For most new designs, external energy is required to achieve healing. For example, thermally reversible covalent bonds or non-covalent supramolecular linkages were introduced into polymers, which upon heating can reversibly rupture and reform to afford self-healing (11). Recently, a metallo-supramolecular polymer was shown to be thermally mendable by converting photo energy into localized heat. In this microphase-separated system, the metal complex healing motifs reside in the crystalline hard domain, which requires thermal energy to reversibly dissociate in order to heal (12). For many applications, however, autonomic healing without any external stimulus is desirable. Toward this goal, an elegant dynamic supramolecular approach was developed to achieve a self-healing rubber by employing multivalent hydrogen bonds, which though individually weak, collectively form a load-bearing network that is dynamic at room temperature, allowing automatic healing of damage. However, the lack of molecular/nano-level structure control severely limits both mechanical properties and processing of this system (13).

SUMMARY

This application generally relates to synthetic engineering materials; more particularly to novel methods to obtain easily processable multifunctional bulk and coating materials by employing a modular, dynamic-matrix nanocomposite approach. This application also relates to a general method for obtaining tunable nanocomposites with multifunctional emergent properties, such as spontaneous self-healing and/or stress-triggered photonic response.

Thus, in one aspect, a method of obtaining a polymeric or nanocomposite material is provided. The method includes assembling a multiphase hard-soft structure, where the structure includes a hard micro- or nano-phase, and a soft micro- or nano-phase that includes a polymeric scaffold. In the method, the polymeric scaffold includes dynamically interacting motifs and has a glass transition temperature ($T_g$) lower than the intended operating temperature of the material.

In some embodiments of the method, the hard phase can be an amorphous or crystalline assembly of oligomers or polymers having a melting temperature ($T_m$) or a $T_g$ higher than the intended operating temperature of the material, or can be preformed micro- or nano-objects selected from the group consisting of spheres, cubes, fibrils, rods and sheets, or a combination thereof. The micro- or nano-objects can be organic, inorganic or metallic micro- or nano-objects, or a combination thereof. In the method, the soft phase and/or its polymeric scaffold can include a linear, branched, hyper-branched or dendritic polymeric structure, or a combination thereof.

In some embodiments of the method, including embodiments described above, the dynamically interacting motifs can be supramolecular interaction motifs that includes mono-dentate or multi-dentate hydrogen bonding groups, ionic interacting groups, pi-pi stacking groups, metal-ligand interacting groups, or hydrophobic interacting groups. Or the dynamically interacting motifs can be dynamic covalent motifs that include covalent bonds capable of dynamically exchanging with or without the aid of a catalyst, external trigger, or energy input under conditions of use.

In some embodiments of the method, including embodiments described above, the hard phase comprises an amorphous or crystalline assembly of oligomers or polymers, and the soft phase and/or its polymeric scaffold comprises oligomers or polymers grafted to the hard phase and containing monovalent or multivalent dynamic non-covalent motifs.

In some embodiments of the method, including embodiments described above, the assembling can include: a) obtaining an oligomer or polymer for formation of the hard phase, the oligomer or polymer having a $T_m$ or $T_g$ higher than the intended operating temperature of the material and including functional groups for attachment to the polymeric scaffold; b) preparing oligomeric or polymeric macromolecules attached to the oligomer or polymer by growth of the macromolecules from the oligomer or polymer, or by attachment of pre-synthesized macromolecules to the oligomer or polymer, where the macromolecules include monomers bearing the dynamically interacting motifs; and c) processing the oligomeric or polymeric macromolecules attached to the oligomer or polymer to produce the multiphase hard-soft structure. The macromolecules can be chemically or physically attached to the oligomer or polymer.

In some embodiments of the method, including embodiments described above, the assembling can include: a) obtaining a micro- or nano-object for formation of the hard phase, the micro- or nano-object containing functional groups for attachment to the polymeric scaffold; b) preparing oligomeric or polymeric macromolecules attached to the micro- or nano-object by growth of the macromolecules from the micro- or nano-object, or by attachment of pre-synthesized macromolecules to the micro- or nano-object, where the macromolecules include monomers bearing the dynamically interacting motifs; and c) processing the oligomeric or polymeric macromolecules attached to the micro- or nano-object to produce the multiphase hard-soft structure. The macromolecules can be chemically or physically attached to the oligomer or polymer.

In some embodiments of the method, including embodiments described above, the hard phase can be prepared from a polymer having a $T_m$ or $T_g$ higher than the intended operating temperature of the material, and which assembles into a spherical, cylindrical, or other microstructure upon processing. Also, the soft phase and/or its polymeric scaffold can include homo-oligomers or homo-polymers that include dynamically interacting motifs, co-oligomers or co-polymers that include different dynamically interacting motifs, or co-oligomers or co-polymers that include dynamically interacting motifs and an additional functional co-monomer.

In some embodiments of the method, including embodiments described above, the hard phase can include inorganic particles or nanoparticles, and the soft phase and/or its polymeric scaffold can include homo-oligomers or homo-polymers that include dynamically interacting motifs, co-oligomers or co-polymers that include different dynamically interacting motifs, or co-oligomers or co-polymers that include dynamically interacting motifs and an additional functional co-monomer.

In some embodiments of the method, including embodiments described above, the hard phase can include micro-carbon or nano-carbon materials and the soft phase and/or its polymeric scaffold can be covalently-linked to the micro-cabon or nano-carbon materials and include homo-oligomers or homo-polymers that include dynamically interacting motifs, co-oligomers or co-polymers include different dynamically interacting motifs, or co-oligomers or co-polymers that include dynamically interacting motifs and an additional functional co-monomer.

In some embodiments of the method, including embodiments described above, the hard phase can include synthetic or bio-derived organic nano-objects, and the soft phase and/or its polymeric scaffold can be covalently-linked to the nano-objects and include homo-oligomers or homo-polymers that include dynamically interacting motifs, co-oligomers or co-polymers that include different dynamically interacting motifs, or co-oligomers or co-polymers that include dynamically interacting motifs and an additional functional co-monomer.

In some embodiments of the method, including embodiments described above, the soft phase and/or its polymeric scaffold can include oligomers or polymers that include dynamically interacting motifs as well as latent covalent cross-linking functional groups which form permanent covalent connections in the soft phase.

In some embodiments of the method, including embodiments described above, the soft phase and/or its polymeric scaffold can include oligomers or polymers that include dynamically interacting motifs as well as a filler or other soft-phase reinforcement material.

In some embodiments of the method, including embodiments described above, the soft phase and/or its polymeric scaffold can include co-oligomers or co-polymers that include dynamically interacting motifs and one or more non-DIM functional monomers.

In some embodiments, including embodiments described above, the hard phase can be an amorphous or crystalline organic phase typically composed of assembled or aggregated polymeric species (such as, but not limited to, styrene, polynorbornene, or polycarbonate) resulting in ordered or disordered nano and/or micro structures with one or more domain dimensions in the range of 1-1000 nm. In these embodiments, the polymer structure of the hard phase may have an additional function beyond its structural role, such as photo-catalysis or other light harvesting energy transduction mechanism. In some embodiments, the hard phase can be amorphous or crystalline particles, typically composed of carbon, metal, or metal-salt compounds, or combinations thereof, which typically have a spheroidal, rod-like, or plate-like form-factor, where the chosen order and orientation of the particles relative to one another may lead to enhanced functionality. In these embodiments, the atomic structure of the particles may be chosen to have an additional function beyond its structural role, such as magnetic response or electronic switching.

In some embodiments, including embodiments described above, the soft phase and/or its polymeric scaffold can be an amorphous polymer such as, but not limited to, acrylic, polyvinyl, polysiloxane, polyester, or polyethylene, in which a DIM such as, but not limited to, a hydrogen bonding alcohol group is built into the polymer structure during or after polymer synthesis. In these embodiments, the polymer may have other motifs such as, but not limited to, chromophores or quaternary ammoniums, which provide additional function such as light harvesting or a bacteriocidal property.

In another aspect, polymeric or composite materials made by the method or any embodiment of the method are provided herein.

BRIEF DESCRIPTION OF THE DRAWINGS

For a more complete understanding of the present invention, reference is now made to the following descriptions taken in conjunction with the accompanying drawings, in which.

DETAILED DESCRIPTION

The following applications are incorporated by reference herein: U.S. Provisional Patent Application Nos. 61/608,029, filed on Mar. 7, 2012, and 61/608,045, filed on Mar. 7, 2012.

Figure 1:
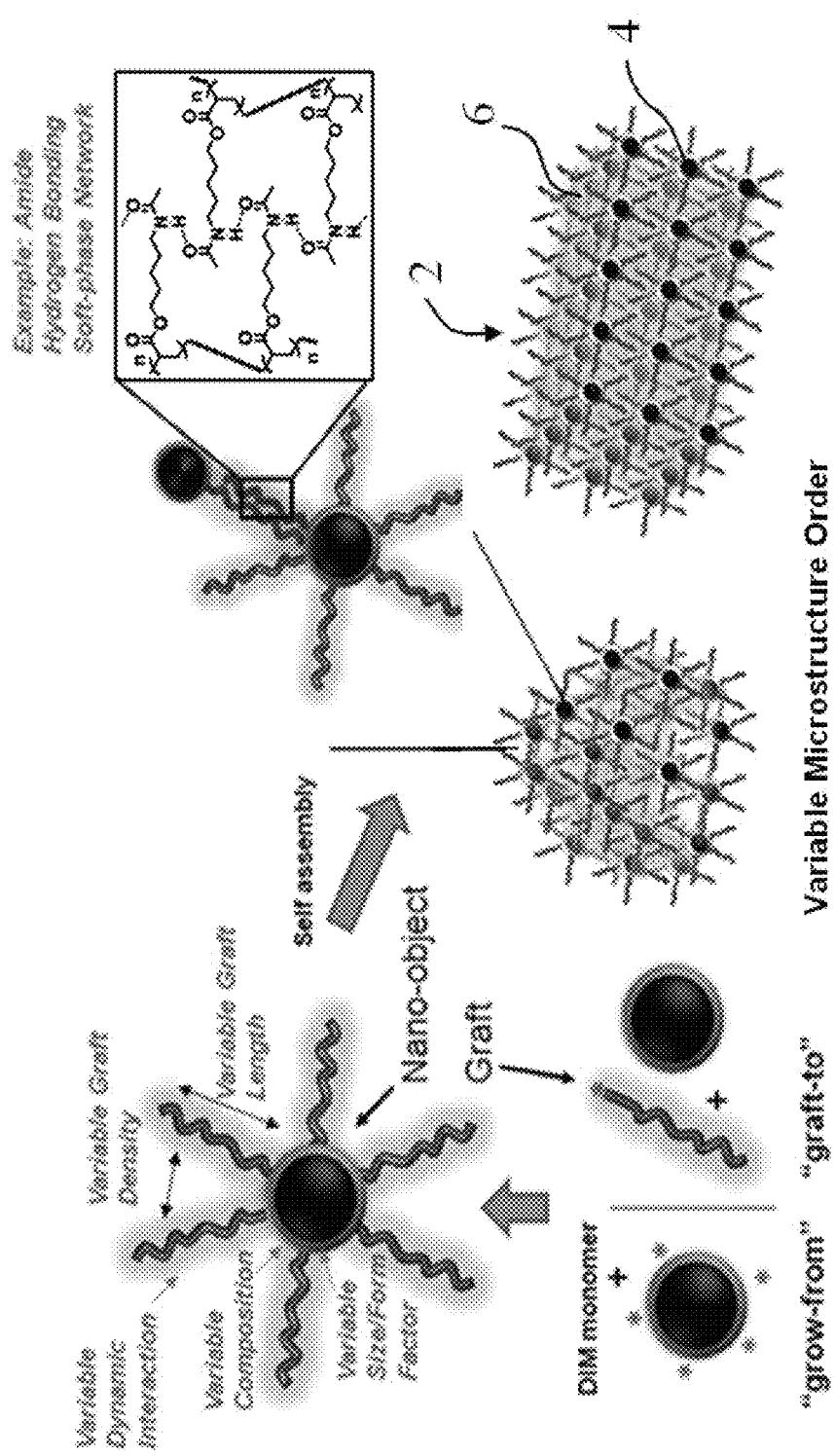
FIG. 1 is a schematic drawing representing the general concept of the method.

In one aspect, a method for obtaining polymeric or composite materials is provided. Referring to FIG. 1, the material can be a dynamic/adaptive, stiff, strong, tough, and/or self-healing polymeric or composite material prepared by programmed assembly of a multiphase (two or more than two micro- or nano-phases) hard-soft micro- or nanostructure 2, where the "hard" micro- or nano-phase 4 is an amorphous or crystalline assembly of oligomers or polymers, in which case they possesses a melting temperature ($T_m$) or glass transition temperature ($T_g$) that is higher than the intended operating temperature of use, or a pre-formed organic or inorganic or metallic micro- or nano-object, selected from a group consisting of spheres, cubes, fibrils, rods, and sheets; whereas the "soft" micro- or nano-phase 6 comprises a linear, branched, hyper-branched, or dendritic polymeric scaffold containing dynamically-interacting motifs (DIMs), with a $T_g$ that is lower than the intended operating temperature of use As used here, a microstructure comprises a hard phase structure having one, two or three dimensions of less than 100 μm but more than 1 μm. As used here, a nanostructure comprises a hard phase structure having one, two or three dimensions of less than 1 μm.

In some embodiments: a) the $T_m$ and $T_g$ for the hard phase oligomers or polymers can range from −50° C. to 350° C.; b) the intended operating temperature of use can be in the range of −100° C. to 300° C.; c) the $T_g$ for the soft phase polymers can be in the range from −150° C. to 250° C.

Examples of oligomers and polymers for use in the hard phase include, but are not limited to, styrene, polynorbornene, and polycarbonate. Examples of oligomers and polymers for use in the soft phase include, but are not limited to, acrylic, polyvinyl, polysiloxane, polyester, and polyethylene.

The dynamically-interacting motifs are molecular fragments which possess an atomic structure such that an attractive force (potential) is felt between the motifs, inducing them to stick or bond to each other when in proximity. The energy of this bond is typically less than 150 kJ/mol, such that bonds spontaneously rupture and reform at operating temperatures. When there are enough DIMs, even though at any time many are un-bonded, enough are bonded to give the material the robust network mechanical properties of a classical rubber. When a bulk material with a continuous DIM network is cut, the atomic-scale reversible adhesion behavior of the DIMs results in network repair and the effective reversal of damage. Examples of the dynamically-interacting motifs include, but are not limited to, any kind of supramolecular interaction motifs including, but not limited to, mono-dentate or multi-dentate hydrogen bonding groups such as hydroxyl, amide, or urea; ionic interacting groups such oxide-ammonium salts; pi-pi stacking groups such as benzenes, naphthalenes, pyrenes, or perylenes; metal-ligand interacting groups such as zinc-imidazole or palladium-pyridine; and hydrophobic interacting groups such as dodecyl or octadecyl. The dynamically-interacting motifs can also be any dynamic covalent motifs such as diels-alder adducts, disulfide bonds, or triazole azide-alkyne cylcoproducts, where covalent bonds can dynamically exchange under the use condition, either with or without the aid of any catalyst, external trigger, or energy input.

Examples of organic, inorganic or metallic micro- or nano-objects include, but are not limited to, carbon black, amorphous silica, carbon nanotubes, magnetite nanoparticles, gold nanorods, and cadmium salt quantum dots.

In some embodiments, the hard phase is an amorphous or crystalline assembly of oligomers or polymers and the soft phase grafted to the hard phase comprises oligomers or polymers containing monovalent or multivalent DIMs. Examples of the oligomers or polymers include, but are not limited to, polystyrene and polyethylene; examples of the dynamically-interacting motifs include, but are not limited to, 2-hydroxyethyl acrylate (HEA) and 5-acetamidopentyl acrylate.

In some embodiments, the assembling includes: a) Synthesizing or acquiring an oligomer or polymer/copolymer having a relatively high $T_m$ or $T_g$, or an organic and/or inorganic nano-object, which will serve as the hard micro- or nanophase and presents any form of latent reactive functionality, to enable connection to the soft phase polymer. A relatively high $T_m$ or $T_g$ is a $T_m$ or $T_g$ above the intended operating temperature of use for the material. The term "latent reactive functionality" means a chemical structure designed to react during the grafting process, but is able to survive and does not interfere with polymer synthesis. b) Synthesizing or acquiring oligomeric or polymeric macromolecules, either grown directly from the hard phase polymer/object, or pre-synthesized then attached to the hard phase in the grafting process, which are comprised fully or partially of monomers bearing any of the dynamically-interacting motifs described herein, according to procedures known to those skilled in the art. The grafts may be attached chemically (covalently; examples including but not limited to polymerization initiators such as, but are not limited to, either "living" or "free-radical" initiators chain transfer agents, or latent "click" functionality) or physically (non-covalently; examples including but not limited to the DIM functionality described herein) connected to end(s) and/or backbone of the polymer or the surface of the nano-object synthesized or chosen in a). c) Processing the material obtained in b) by any process known in the art, such as but not limited to, casting, molding, injection, spinning, melt extrusion, or additive manufacturing techniques. This results in the desired multiphase material.

In some embodiments, the hard phase is derived from a relatively high $T_g$ or $T_m$ polymer, which assembles into a spherical, cylindrical, or other microstructure upon processing, and the soft phase comprises homo-oligomers or homo-polymers of a single DIM, co-oligomers or co-polymers of different DIMs, or co-oligomers or co-polymers of DIMs and one more functional co-monomer. A "functional co-monomer" is a chemical structure built into the soft phase polymer not to display a dynamic interaction, but for some other purpose, such as a chromophore for light harvesting or a quaternary ammonium for bacteriocidal effect.

In some embodiments, the hard phase comprises one type or multiple types of inorganic particles or nanoparticles; for example one type may absorb photonic energy and transfer it to a different type, where it may be used to catalyze a chemical reaction, or a mixture of form factors such as cylindrical and plate like delivers enhanced, anisotropic, non-linear mechanical or opto-electronic function. Examples of inorganic particles include, but are not limited to, silica particles, carbon black, micronized salts, and pigments. Examples of nanoparticles include, but are not limited to, insulating nanoparticles such as silica ($SiO_2$), magnetite ($Fe_2O_3$), alumina ($Al_2O_3$); semiconducting nanoparticles such as titania ($TiO_2$), cadmium selenide (CdSe), lead selenide (PbSe); conducting nanoparticles such as gold (Au) or silver (Ag). These inorganic particles and nanoparticles can be monodisperse (<10% size variation) or vary widely in size (>10% variation), and can possess any form factor such as spheroidal, cylindrical, or platelet. Also, the soft phase comprises homo-oligomers or homo-polymers of a single DIM, co-oligomers or co-polymers of different DIMs, or co-oligomers or co-polymers of DIMs and one more functional co-monomer. The surface density of nanoparticle grafting may be varied according to procedures known in the art, and grafts of different composition or function may be combined on the same nanoparticle.

In some embodiments, the hard phase is a "micro-carbon" (such as, but not limited to, carbon black or graphite) or "nano-carbon" material (such as, but not limited to, C60, graphene, or carbon nanotube). Also, the covalently-linked soft phase comprises homo-oligomers or homo-polymers of a single DIM, co-oligomers or co-polymers of different DIMs, or co-oligomers or co-polymers of DIMs and one more functional co-monomer.

In some embodiments, the hard phase is a synthetic or bio-derived organic nano-object (such as, but not limited to, polyaniline or hydroxycellulose whiskers) and the covalently-linked soft phase comprises homo-oligomers or homo-polymers of a single DIM, co-oligomers or co-polymers of different DIMs, or co-oligomers or co-polymers of DIMs and one more functional co-monomers.

In some embodiments, the hard phase can be any hard phase described herein and the soft phase comprises oligomers or polymers of DIMs as well as latent covalent cross-linking functionality, which is subsequently reacted to add some permanent covalent connections to the soft phase. The term "latent covalent cross-linking functionality" means chemical structures that react to form a permanent network only after material processing, or in response to external stimuli such as light or heat. For example, epoxide will react with an alcohol group in the presence of a cationic photoinitiator.

In some embodiments, the hard phase can be any hard phase described herein and the soft phase comprises oligomers or polymers of DIMs as well as a filler (such as, but not limited to, carbon black or fused silica), or other means of soft-phase reinforcement (such as, un-grafted nano-objects like silica nanoparticles or C60.

In some embodiments, the hard phase can be any hard phase described herein and the soft phase comprises co-oligomers or co-polymers of DIMs with one or more non-DIM functional monomers (examples of such functional monomers include, but are not limited to, long-chain aliphatics for side-chain crystallinity and temperature responsive mechanical properties, and/or quaternary ammonium groups for anti-bacterial effects).

The present invention may be better understood by referring to the accompanying examples, which are intended for illustration purposes only and should not in any sense be construed as limiting the scope of the invention.

Example 1

5-acetylaminopentyl acrylate. 5-Acetamido-1-pentanol (A. Temperini, R. Terlizzi, L. Testaferri, M. Tiecco, *Synth. Commun.* 40, 295 (2010), incorporated by reference herein) (26.6 g, 183 mmol) was added to a solution of acrylic acid (19.8 g, 275 mmol), EDC.HCl (57.9 g, 302 mmol) and DIPEA (39.0 g, 302 mmol) in DCM (500 mL). The mixture was stirred at room temperature for 24 h. Another 500 mL DCM was added and the mixture was washed sequentially with 1 M NaOH, 1 M HCl, saturated NaHCO$_3$ and brine. The organic phase was dried over Na$_2$SO$_4$, filtered, and the solvent was removed under reduced pressure. The crude product was purified by flash chromatography (99:1 DCM: Methanol), and the pure fractions combined and evaporated to give 32.70 g (90%) of (1). $^1$H NMR (500 MHz, DMSO-d$_6$, 298 K) δ 7.79 (s, 1H), 6.32 (dd, J=17.3, 1.4, 1H), 6.17 (dd, J=17.3, 10.3, 1H), 5.93 (dd, J=10.3, 1.4, 1H), 4.09 (t, J=6.6, 2H), 3.01 (dd, J=12.8, 6.6, 2H), 1.77 (s, 3H), 1.57-1.63 (m, 2H), 1.37-1.41 (m, 2H), 1.28-1.33 (m, 2H); $^{13}$C NMR (125 MHz, DMSO-d$_6$, 298 K) δ 168.9, 165.5, 131.4, 128.4, 64.0, 38.3, 28.8, 27.8, 22.9, 22.6; MS (ESI), m/z calcd for [C$_{10}$H$_{17}$NO$_3$+H]$^+$=200.13; found 200.21.

Synthesis of Macroinitiators.

Styrene (1.4060 g, 13.5 mmol), 4-(2-Bromoisobutyloyl-methyl)-styrene (4) (0.4247 g, 1.5 mmol) and AIBN (24.6 mg, 0.15 mmol) were dissolved in 7.5 mL toluene. The mixture was stirred at room temperature for 30 min under nitrogen flow, and then was heated at 70° C. for 48 h. Upon cooling to room temperature, the polymer was precipitated in methanol. Filtered and dried at 60° C. under vacuum to give the macroinitiator. Yield: 71% (1.3075 g). Mn: 13.9 KDa; PDI: 1.67.

Synthesis of Polymer Graft.

Figure 2:
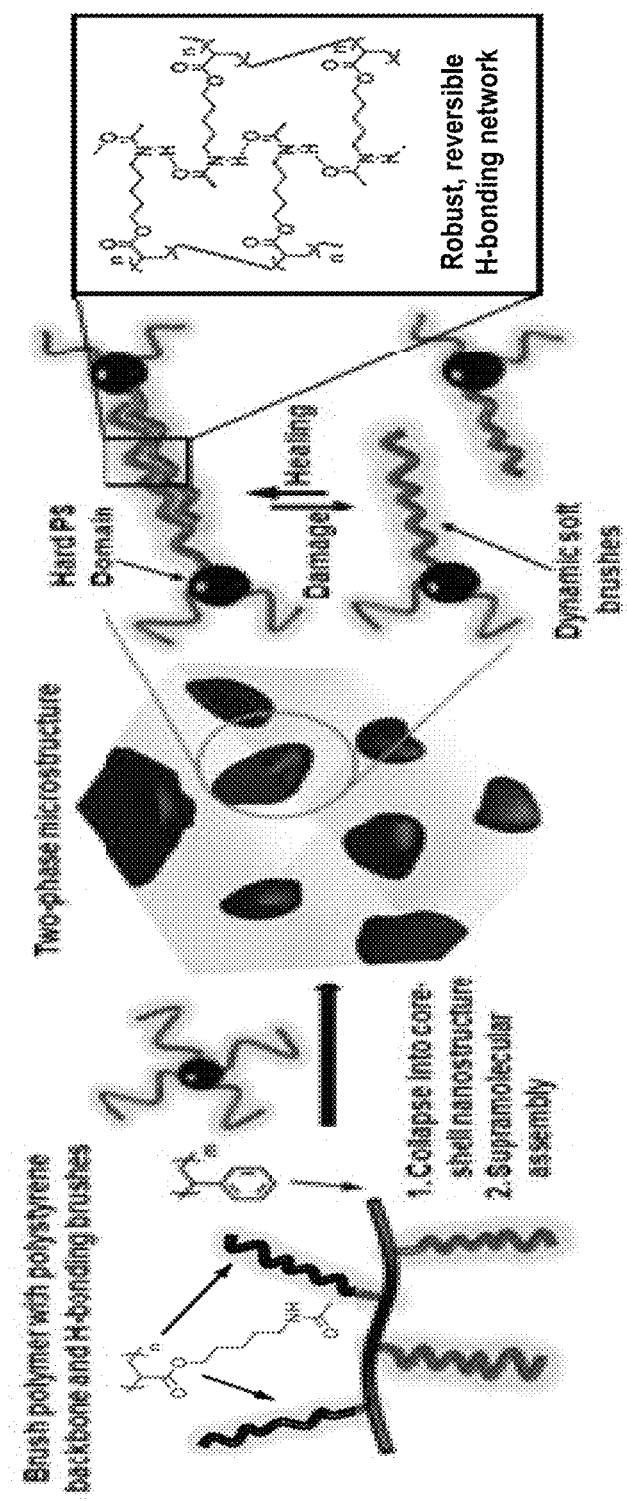
FIG. 2 is a schematic drawing of the process described in Example 1.

The grafted styrene/DIM co-polymers were synthesized according as follows: First, a polystyrene macroinitiator having 10 mol % 4-(2-bromoisobutyloylmethyl)-styrene was synthesized by free radical copolymerization (M$_n$: 13.9 KDa; PDI: 1.67). The macroinitiator (0.098 g, 0.08 mmol Br), 5-acetylaminopentyl acrylate (1) (3.99 g, 20 mmol), and PMDETA (29.4 mg, 0.17 mmol) were dissolved in DMF (10 mL). The mixture was degassed with three freeze-pump-thaw cycles. After addition of CuBr (12.2 mg, 0.085 mmol), the mixture was heated at 70° C. for 24 h. The monomer conversion was determined by $^1$H NMR spectroscopy. Upon cooling, the polymer was precipitated three times in ether to thoroughly remove any residual monomer. Catalyst was removed by passing a solution of the polymer in MeOH over a basic alumina plug. The dried polymer (3.2 g) was obtained by evaporating the methanol solution under vacuum at 110° C. (SEC-MALLS, M$_n$: 435.4 KDa; PDI: 1.26). Both $^1$H NMR spectroscopy and thermogravimetric analysis (TGA) of the dried polymers confirmed that no residual MeOH or water was present in the dried samples. A schematic of the process is shown in FIG. 2.

Morphology Characterization.

TEM was performed on a FEI/Philips CM-20 conventional TEM operated at an accelerating voltage of 200 kV. The polyacrylate amide phase was stained by floating the TEM grid on a 0.5 wt % aqueous solution of uranyl acetate for 1 minute, followed by removing excess solvent by placing the sample on filter paper. SAXS studies were carried out at the Materials Research Laboratory of the University of California, Santa Barbara. Exact details of the homebuilt SAXS setup can be found on the Internet at: mrl.ucsb.edu/mrl/centralfacilities/xray/instruments/saxs.html.

Mechanical Testing.

Figure 3:
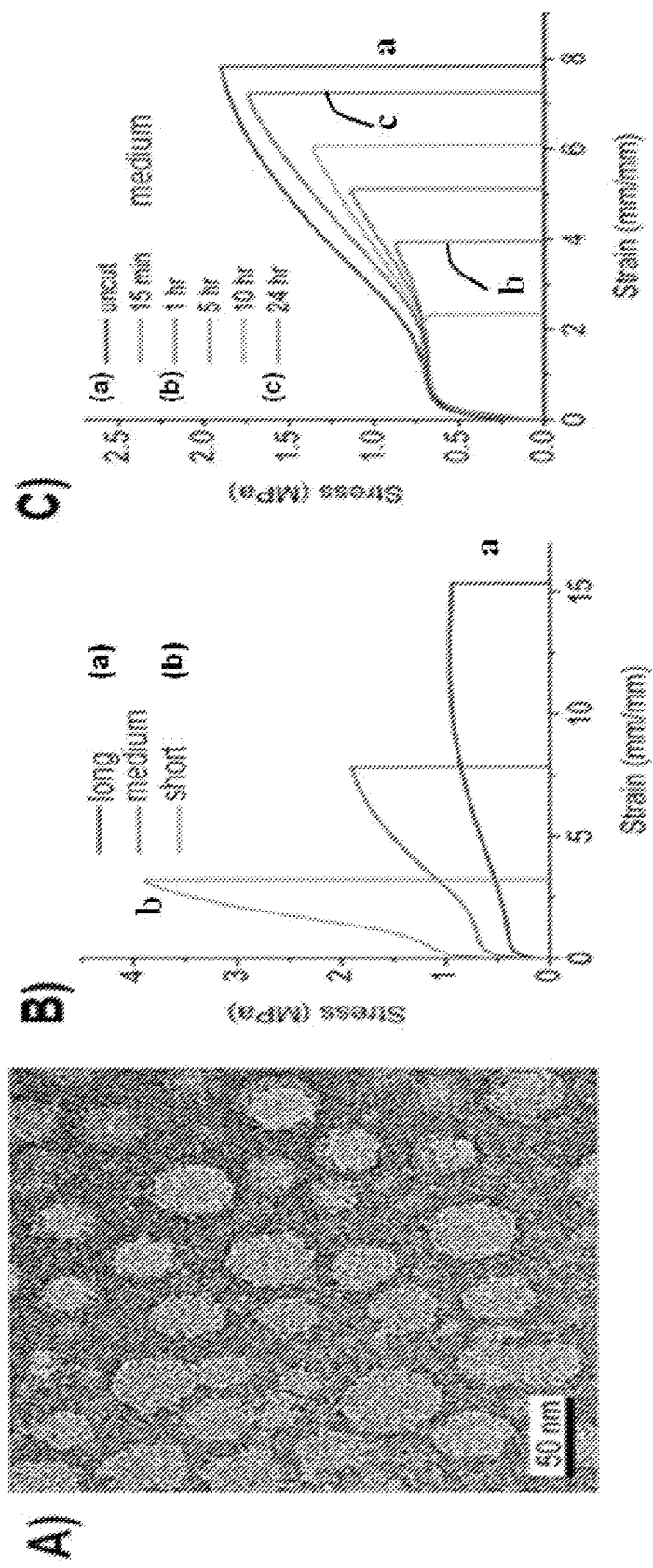
FIG. 3 is a panel showing characteristics of synthesized materials: (A) TEM image showing microstructural morphology of material (light: polystyrene spheroidal hard phase; dark: grafted H-bonding soft phase; (B) tuning mechanical properties by varying graft length and density; (C) Self-healing after catastrophic failure at various healing times. Tensile-test specimens were bisected with a razor blade, then the cut faces re-contacted and allowed to sit for various times before stretching to failure. The stress-strain curves increasingly match that of the pristine uncut sample with increasing healing time, illustrating the dynamic nature of the hydrogen-bond network re-formation process.

The mechanical properties of the copolymers were measured using an Instron 3365 machine in standard stress/strain experiments. Samples were prepared by hot-pressing the resin into Teflon moulds. The specimens were extended at 100 mm/min at room temperature. Each measurement was repeated at least three times. Young's modulus (E) was determined from the initial slope of the stress-strain curves. Creep recovery and stress-relaxation experiments were performed using a TA Instruments DMA Q800 with attached cryo accessory. The films were pulled at a certain stress for 800 min, and then the stress was released and the films were recovered for another 800 min at 25° C. In stress-relaxation tests, the samples were pulled at a rate of 10 or 100 mm/min to reach a 100% strain, which was set at this strain for relaxation for 800 minutes. Rheology data were collected on an AR G2 Rheometer from TA Instruments (20 mm parallel steel plate). Time sweep experiments were performed to obtain the moduli of the materials at 1 Hz and 1% strain at 25° C. FIG. 3A is a TEM image showing the morphology of synthesized materials, and FIG. 3B are stress-strain curves for various materials.

Sample Damaging and Healing Tests.

For self healing tests, a sample was cut into two completely separate pieces. The cut faces were gently pressed together for 1 minute and then the sample was let to heal in a low humidity dessicator (approx. 0% relative humidity using Drierite) at room temperature for various times. The self-healed samples were then subjected to stress-strain tests at room temperature at 100 mm/min pulling rate. FIG. 3C are stress-strain curves of self-healed samples.

Example 2

Figure 4:
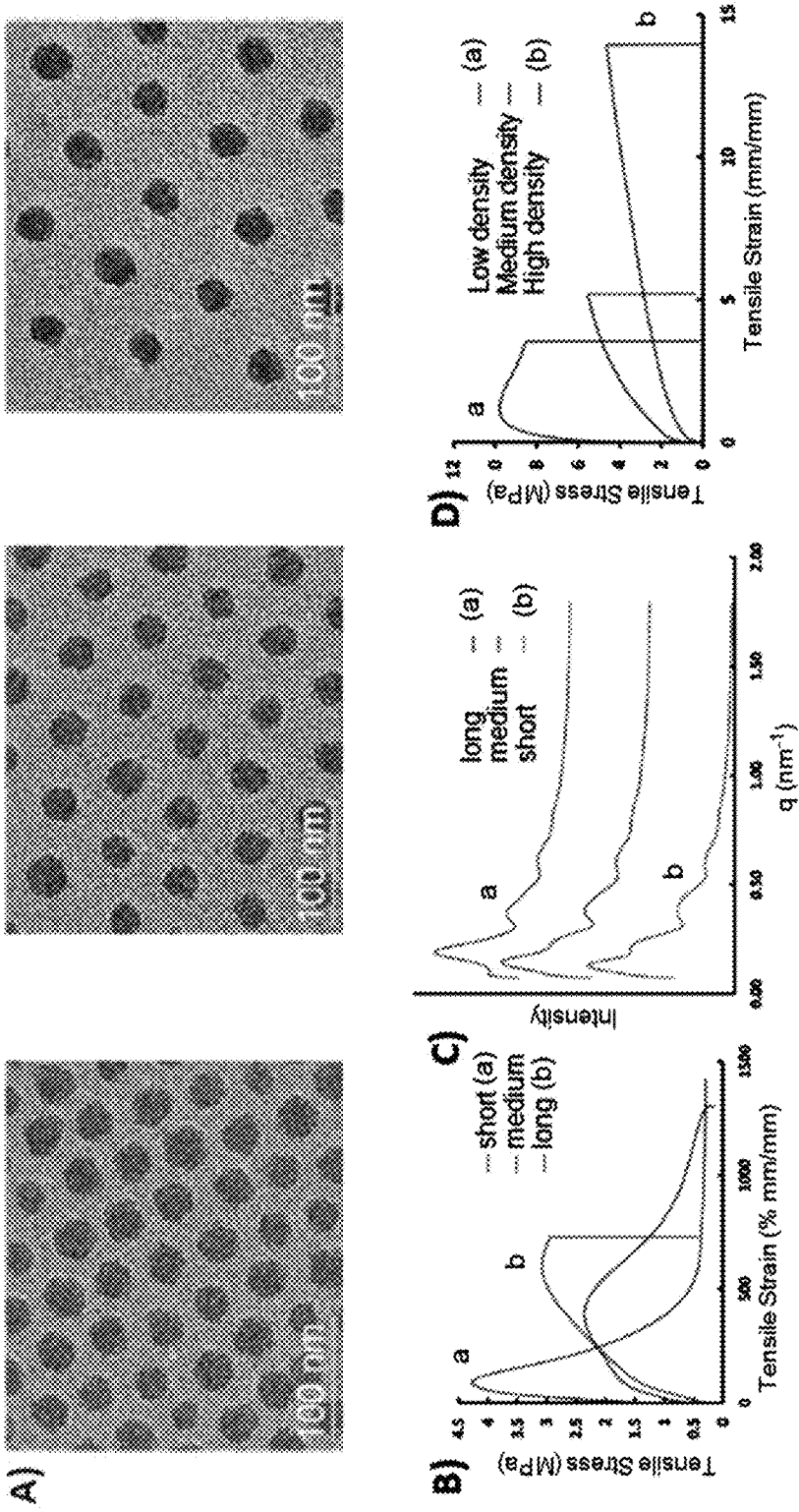
FIG. 4 is a panel showing characteristics of synthesized materials: (A) TEM illustrating variation of graft length for the material; (B) mechanical property tuning by changing graft length; (C) highly ordered nanostructure characteristic of various materials; d) tuning mechanical properties by varying graft density.

DIM polymer grafted nanoparticles with variable chain length. To a flame dried 50 mL Schlenk round bottom was added ATRP silica nanoparticles (0.300 g, 0.104 mmol Br), the compound in Example 1 (2.07 g, 10.41 mmol, 100 equiv), and anhydrous DMF (13 mL). The mixture was then sealed and sonicated for 10 minutes. After sonication, the mixture was degassed with argon for 1 hour while stirring. At this time, CuBr (14.9 mg, 0.104 mmol, 1 equiv) and CuBr$_2$ (11.6 mg, 0.052 mmol, 0.5 equiv) were added. The mixture was degassed for another 15 minutes. PMDETA (61 μL, 0.312 mmol, 3 equiv) was added and the yellow reaction immediately turned blue-green. A small aliquot is taken for monomer conversion measurements by NMR. The mixture is degassed for another 15 minutes. At this time, the reaction is sealed under argon and placed in an oil bath at 50° C. stirring at 730 rpm. After 23 hours, the reaction is removed from heat and the polymerization is terminated by exposing to air. NMR is used to confirm the percent of monomer conversion. The reaction mixture is concentrated in vacuo to a volume of 5 mL and precipitated into stirring diethyl ether. The ether is decanted and saved to recover unreacted monomer, while the hybrid particle precipitate is dissolved in 5 mL methanol and reprecipitated in stirring ether. After removing the unreacted monomer, the hybrid particles are dissolved in DMF and run through an alumina column to remove copper. The DMF is evaporated to give the hybrid particles as a clear gel (0.510 g). FIGS. 4A, 4B and 4C show the structure and characteristics of various materials.

Example 3

DIM polymer grafted nanoparticles with variable graft density. Grace Davison AS-40 colloidal silica (d=30 nm) was received as an aqueous solution (pH=9.1 to 9.7). An AS-40 silica solution (10.0 g silica solution, 4.0 g SiO$_2$, 3.69 mmol OH) was added to a round bottom flask. Separately, 3-(ethoxydimethylsilyl)propyl pivalate (0.289 g, 0.922 mmol) and 3-(ethoxydimethylsilyl)propyl 2-bromo-2-methylpropanoate (1.60 g, 6.45 mmol) were added to 125 mL 60:40 EtOH:H$_2$O. This ethanolic solution was quickly added to the stirring solution of silica nanoparticles. The reaction mixture was stirred for 18 h at 40° C. DMF (50 mL) was then added to the reaction mixture and then ethanol and water were removed in vacuo. After evaporation, the DMF nanoparticle solution was heated at 80° C. for 18 h. The mixture was then cooled to room temperature and precipitated in diethyl ether (100 mL). The nanoparticles were collected by centrifugation at 2500 rpm for 5 minutes. The particles were redissolved in THF, precipitated in hexanes, and collected by centrifugation. This process was repeated 4 times. The nanoparticles were then dried under vacuum at 50° C. for 12 h. Elemental Analysis (Atlantic Microlabs): 0.39 wt % Bromine, 0.31 init/nm2 for radius=15.0 nm. FIG. 4D shows characteristics of various materials.

Example 4

DIM polymer grafted nanoparticles with variable size and emergent properties. Preparation of Monodisperse Silica Nanoparticles. Ethanol (950 mL) was added to a 2 L round bottom flask. While stirring, 25% $NH_4OH$ in water (69.3 g, 1015 mmol $NH_3$) in ethanol (25 mL) was added all at once. After stirring for 10 minutes, TEOS (36.82 g, 167 mmol) in ethanol (25 mL) was added all at once. The mixture was stirred vigorously for 24 h, at which point the particles were collected by centrifugation (8000 rpm, 15 min). The particles were redispersed/recentrifuged in ethanol 3 more times, once in water, and once more in ethanol. The nanoparticles were then dried under vacuum for 12 h at 100° C. to give 10.28 g. Size by TEM analysis: 170±11 nm. Preparation of ATRP Initiator Functionalized Silica Nanoparticles. The dried silica nanoparticles (10.28 g) were dissolved ethanol (854 mL) by ultrasonication. While stirring, 25% $NH_4OH$ (88.2 g) in ethanol (321 mL) was added drop-wise at room temperature. After complete addition of base, the reaction mixture was stirred at 40° C. for 2 hours. At this point, 3-(triethoxysilyl)propyl 2-bromo-2-methylpropanoate (6.49 g, 17.52 mmol) in ethanol (84 mL) was added drop-wise to the reaction mixture. The mixture was then stirred at 40° C. for 24 h. The particles were then collected by centrifugation at 6500 rpm for 20 min. The particles were resuspended/centrifuged in ethanol (4 times) and THF (2 times) to give 8.00 g of functionalized silica nanoparticles. Elemental analysis (Atlantic Microlabs): 0.27 wt % bromine. Typical Procedure for Surface Initiated Atom Transfer Radical Polymerization. Silica nanoparticles (0.500 g, 0.017 mmol), copper (II) bromide (1.9 mg, 0.0085 mmol), amide monomer (3.39 g, 17 mmol), p-dimethoxybenzene (0.100 g, 0.72 mmol), and DMF (1.9 mL) were added to a 25 mL air-free flask. This mixture was then sonicated for 30 minutes to ensure homogeneous dispersion of the materials. The reaction mixture was then stirred under argon flow for 30 minutes, followed by the addition of copper (I) bromide (2.4 mg, 0.017 mmol). The reaction mixture was degassed under argon flow for another 15 minutes. PMDETA (10.2 µL, 0.051 mmol) in 0.2 mL of DMF was separately degassed with argon for 5 minutes and then subsequently added to the reaction mixture. A small aliquot was taken as a reference to determine the conversion of the reaction via NMR. The mixture was degassed another 10 minutes, and then sealed under argon. The reaction mixture was heated at 50° C. until the appropriate percent conversion was reached. The reaction mixture was then diluted in 50 mL MeOH and centrifuged at 8500 rpm for 10 min. The supernatant was saved to recover unreacted monomer. The pellet was redissolved in MeOH and the centrifugation/purification cycles repeated a total of three times.

Description of half-cut self-healing characterization protocol. The sample was cut 50% of the way through and allowed to heal at elevated temperature for 24 hours. Uncut and healed samples were then subjected to a multi-cyclic strain test. Briefly, a sample was strained to 36%, relaxed to 12%, and strained/relaxed in 6% increments until a strain of 80% was reached. Healing was confirmed if the stress/strain curves overlapped perfectly.

Description of strain-photonics characterization protocol. Reflection spectra were recorded using a Perkin Elmer Lambda 950 spectrophotometer coupled to a Perkin Elmer 60 mm Integrating Sphere illuminating an area of 250 mm2. Strain was applied to the sample using a custom setup.

Figure 5:
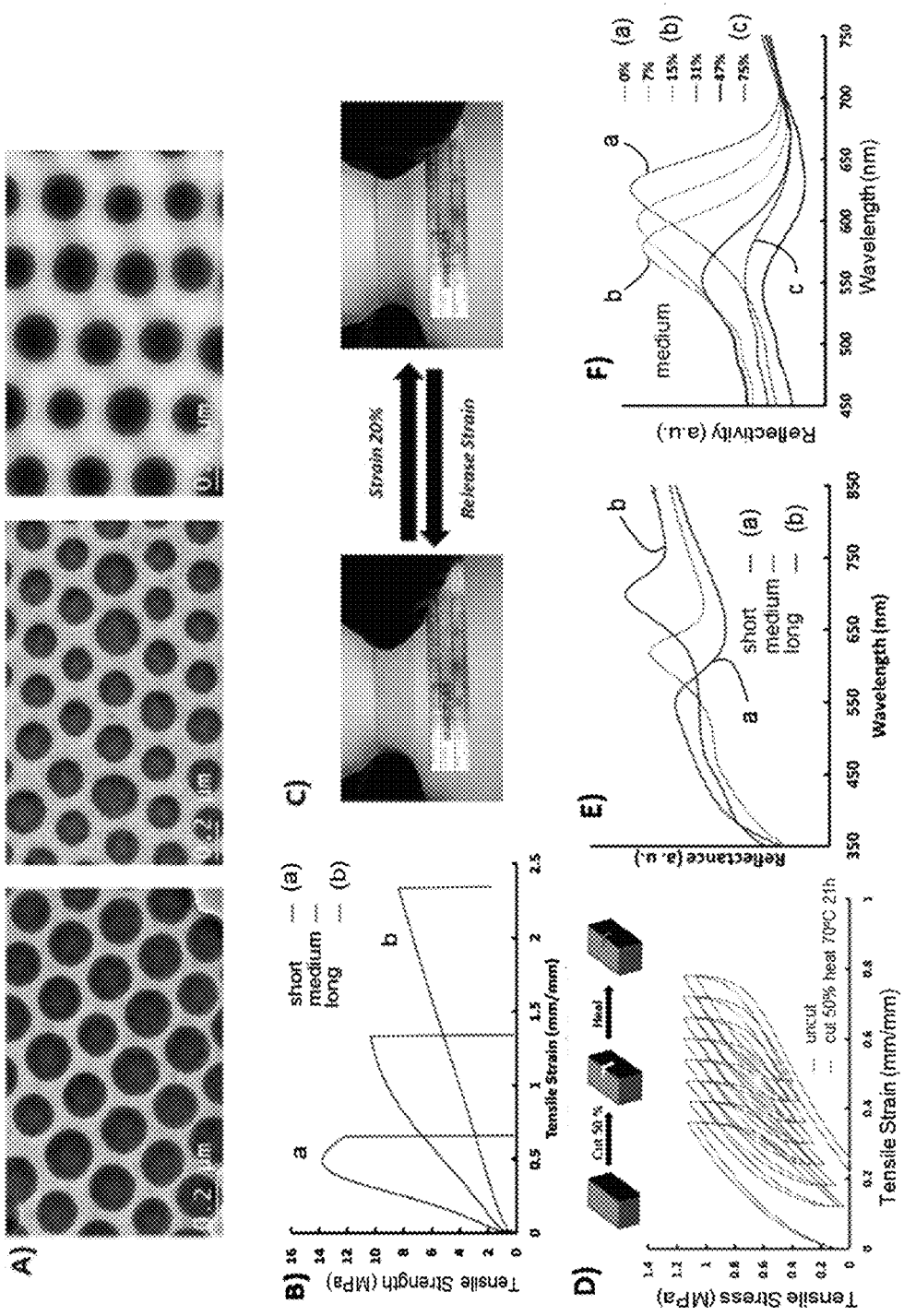
FIG. 5 is a panel showing the structure and characteristics of materials: (A) TEM illustrating variation of graft length for larger particles; (B) mechanical property tuning by changing graft length; (C) photonic effects under strain; (D) full toughness recovery after partial failure and self-healing with mild heating; (E) color variation with interpaticle distance due to photonic-crystal effect; (F) color variation with strain due to photonic-crystal effect

Properties of the synthesized materials are provided in FIG. 5.

REFERENCES

The following publications are incorporated by reference herein:
1. D. H. Middleton, *Composite Materials in Aircraft Structures*, Wiley, 1990.
2. D. L. C. Chung, *Composite Materials: Functional Materials for Modern Technologies*, Springer, 2003.
3. K. Friedrich, S. Fakirov, Z. Zhang, *Polymer Composites: From Nano-to Macro-Scale*, Springer, 2005.
4. Y.-W. Mai, Z.-Z. Yu, *Polymer Nanocomposites*, CRC Press, 2006.
5. B. L. Smith, T. E. Schaffer, M. Viani, J. B. Thompson, N. A. Frederick, J. Kindt, A. Belcher, G. D. Stucky, D. E. Morse, P. K. Hansma, Molecular mechanistic origin of the toughness of natural adhesives, fibres and composites, *Nature* 1999, 399, 761.
6. A. M. Kushner, Z. Guan, Modular Design in Natural and Biomimetic Soft Materials, *Angewandte Chemie International Edition* 2011, 50, 9026.
7. A. Miserez, T. Schneberk, C. Sun, F. W. Zok, J. H. Waite, The Transition from Stiff to Compliant Materials in Squid Beaks, *Science* 2008, 319, 1816.
8. J. R. Capadona, K. Shanmuganathan, D. J. Tyler, S. J. Rowan, C. Weder, Stimuli-Responsive Polymer Nanocomposites Inspired by the Sea Cucumber Dermis, *Science* 2008, 319, 1370.
9. M. W. Urban, Dynamic Materials: The Chemistry of Self-healing, *Nat. Chem.* 2012, 4, 80.
10. S. R. White, N. R. Sottos, P. H. Geubelle, J. S. Moore, M. R. Kessler, S. R. Sriram, E. N. Brown, S. Viswanathan, Autonomic healing of polymer composites, *Nature* 2001, 409, 794.
11. X. Chen, M. A. Dam, K. Ono, A. Mal, H. Shen, S. R. Nutt, K. Sheran, F. Wudl, A Thermally Re-mendable Cross-Linked Polymeric Material, *Science* 2002, 295, 1698.
12. M. Burnworth, L. Tang, J. R. Kumpfer, A. J. Duncan, F. L. Beyer, G. L. Fiore, S. J. Rowan, C. Weder, Optically healable supramolecular polymers, *Nature* 2011, 472, 334.
13. P. Cordier, F. Tournilhac, C. Soulie-Ziakovic, L. Leibler, Self-healing and Thermoreversible Rubber from Supramolecular Assembly, *Nature* 2008, 451, 977.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:
1. A method of obtaining a polymeric or composite material, comprising assembling a multiphase hard-soft structure that comprises
  a hard microphase, and
  a soft micro- or nano-phase comprising a polymeric scaffold,
wherein the polymeric scaffold comprises dynamically interacting motifs and has a glass transition temperature ($T_g$) lower than the intended operating temperature of the material,
wherein the hard phase comprises an amorphous or crystalline assembly of oligomers or polymers having a melting temperature (Tm) or a Tg higher than the intended operating temperature of the material,
wherein the dynamically interacting motifs are supramolecular interaction motifs comprising mono-dentate or multi-dentate hydrogen bonding groups, ionic interacting groups, pi-pi stacking groups, metal-ligand interacting groups, or hydrophobic interacting groups,
wherein the soft phase is covalently linked to the hard phase,
wherein the Tm and Tg for the hard phase oligomers or polymers is in the range of −50° C. to 350° C., the intended operating temperature of use is in the range of −100° C. to 300° C., and the Tg for the soft phase polymers is in the range of −150° C. to 250° C., and
wherein the hard phase is prepared from a polymer which assembles into a spherical or cylindrical microstructure upon processing, and the soft phase comprises homo-oligomers or homo-polymers comprising dynamically interacting motifs, co-oligomers or co-polymers comprising different dynamically interacting motifs, or co-oligomers or co-polymers comprising dynamically interacting motifs and an additional functional co-monomer.

2. The method of claim 1, wherein the soft phase comprises a linear, branched, hyper-branched or dendritic polymeric structure, or a combination thereof.

3. The method of claim 2, wherein the soft phase comprises acrylic, polyvinyl, polysiloxane, polyester or polyethylene.

4. The method of claim 1, wherein the hard phase comprises styrene, polynorbornene or polycarbonate.

5. The method of claim 1, wherein the assembling comprises:
  obtaining an oligomer or polymer for formation of the hard phase, the oligomer or polymer comprising functional groups for attachment to the polymeric scaffold;
  preparing oligomeric or polymeric macromolecules attached to the oligomer or polymer by growth of the macromolecules from the oligomer or polymer, or by attachment of pre-synthesized macromolecules to the oligomer or polymer, wherein the macromolecules comprise monomers bearing the dynamically interacting motifs; and
  processing the oligomeric or polymeric macromolecules attached to the oligomer or polymer to produce the multiphase hard-soft structure.

6. The method of claim 1, wherein the soft phase comprises oligomers or polymers comprising dynamically interacting motifs as well as latent covalent cross-linking functional groups which form permanent covalent connections in the soft phase.

7. The method of claim 1, wherein the soft phase comprises oligomers or polymers comprising dynamically interacting motifs as well as a filler or other soft-phase reinforcement material.

8. The method of claim 1, wherein the soft phase comprises co-oligomers or co-polymers comprising dynamically interacting motifs and one or more non-DIM functional monomers.

9. The method of claim 1, wherein the Tm and the Tg of the hard phase is higher than the Tg of the soft phase.

10. The method of claim 1, wherein the spherical or cylindrical microstructure is a structure with one or more domain dimensions in the range of 1-1000 nm.

11. The method of claim 1, wherein the hard phase comprises preformed micro- or nano-objects selected from the group consisting of spheres, cubes, fibrils, rods and sheets, and a combination thereof.

12. A nanocomposite material which is self-healing at an intended operating temperature and which is a multiphase hard-soft structure that comprises:
  a hard micro- or nano-phase, and
  a soft micro- or nano-phase comprising a polymeric scaffold having dynamically interacting motifs,
  wherein the soft phase has a glass transition temperature (Tg) lower than the intended operation temperature of the material,
  wherein the hard phase comprises (i) an amorphous or crystalline assembly of oligomers or polymers having a melting temperature (Tm) higher than the intended operating temperature of the material, or (ii) an amorphous or crystalline assembly of oligomers or polymers having a Tg higher than the intended operating temperature of the material, or (iii) a preformed micro- or nano-object selected from the group consisting of spheres, cubes, fibrils, rods, and sheets, or (iv) a combination thereof,
  wherein the soft phase is covalently linked to the hard phase,
  wherein the Tm and Tg for the hard phase oligomers or polymers is in the range of −50° C. to 350° C., the intended operating temperature of use is in the range of −100° C. to 300° C., and the Tg for the soft phase polymers is in the range of −150° C. to 250° C., and
  wherein the dynamic interacting motifs are supramolecular interaction motifs comprising a metal-ligand interacting group, and the metal-ligand interacting group comprises an imidazole moiety and a metal cation.

13. A composite material which is self-healing at an intended operating temperature and which is a multiphase hard-soft structure that comprises:
  a hard micro- or nano-phase, and
  a soft micro- or nano-phase comprising a polymeric scaffold having dynamically interacting motifs,
  wherein the soft phase has a glass transition temperature (Tg) lower than the intended operation temperature of the material,
  wherein the dynamically interacting motifs are supramolecular interaction motifs comprising at least one of mono-dentate or multi-dentate hydrogen bonding groups, ionic interaction groups, pi-pi stacking groups, metal-ligand interacting groups, or hydrophobic interacting groups,
  wherein the hard phase comprises (i) an amorphous or crystalline assembly of oligomers or polymers having a melting temperature (Tm) higher than the intended operating temperature of the material, or (ii) an amorphous or crystalline assembly of oligomers or polymers having a Tg higher than the intended operating temperature of the material, or (iii) a preformed micro- or nano-object selected from the group consisting of spheres, cubes, fibrils, rods, and sheets, or (iv) a combination thereof, wherein the soft phase is covalently linked to the hard phase, wherein the Tm and Tg for the hard phase oligomers or polymers is in the range of −50° C. to 350° C., the intended operating temperature of use is in the range of −100° C. to 300° C., and the Tg for the soft phase polymers is in the range of −150° C. to 250° C., and wherein the hard phase is prepared from a polymer which assembles into a spherical or cylindrical microstructure upon processing when the hard phase comprises (i) or (ii), and wherein the soft phase comprises homo-oligomers or homo-polymers comprising dynamically interacting motifs, co-oligomers or co-polymers comprising different dynamically interacting motifs, or co-oligomers or co-polymers comprising dynamically interacting motifs and an additional functional co-monomer.

14. A nanocomposite material which is self-healing at an intended operating temperature and which is a multiphase hard-soft structure that comprises:
a hard micro- or nano-phase, and
a soft micro- or nano-phase comprising a polymeric scaffold having dynamically interacting motifs,
wherein the soft phase has a glass transition temperature (Tg) lower than the intended operation temperature of the material, wherein the hard phase comprises (i) an amorphous or crystalline assembly of oligomers or polymers having a melting temperature (Tm) higher than the intended operating temperature of the material, or (ii) an amorphous or crystalline assembly of oligomers or polymers having a Tg higher than the intended operating temperature of the material, or (iii) a preformed micro- or nano-object selected from the group consisting of spheres, cubes, fibrils, rods, and sheets, or (iv) a combination thereof, wherein the soft phase is covalently linked to the hard phase, wherein the Tm and Tg for the hard phase oligomers or polymers is in the range of −50° C. to 350° C., the intended operating temperature of use is in the range of −100° C. to 300° C., and the Tg for the soft phase polymers is in the range of −150° C. to 250° C., and wherein the dynamic interacting motifs are supramolecular interaction motifs comprising a metal-ligand interacting group, and the metal-ligand interacting group comprises a pyridine moiety and a metal cation.

* * * * *